United States Patent
Conrad et al.

(10) Patent No.: US 6,250,307 B1
(45) Date of Patent: Jun. 26, 2001

(54) SNORING TREATMENT

(75) Inventors: Timothy R. Conrad, Eden Prairie; Mark B. Knudson, Shoreview, both of MN (US); Jerry C. Griffin, Chicago, IL (US)

(73) Assignee: Pi Medical, Inc., St. Paul, MN (US)

( * ) Notice: Subject to any disclaimer, the term of this patent is extended or adjusted under 35 U.S.C. 154(b) by 0 days.

(21) Appl. No.: 09/398,991

(22) Filed: Sep. 17, 1999

(51) Int. Cl.[7] .................................................... A61B 19/00

(52) U.S. Cl. .............................................................. 128/898

(58) Field of Search ..................................... 128/898, 897; 600/12

(56) References Cited

U.S. PATENT DOCUMENTS

| | | |
|---|---|---|
| Re. 36,120 | 3/1999 | Karell . |
| 3,998,209 | 12/1976 | Macvaugh . |
| 4,978,323 * | 12/1990 | Freedman ............................... 600/12 |
| 5,046,512 | 9/1991 | Murchie . |
| 5,052,406 | 10/1991 | Tepper . |
| 5,133,354 | 7/1992 | Kallock . |
| 5,176,618 * | 1/1993 | Freedman ............................... 600/12 |
| 5,178,156 | 1/1993 | Takishima et al. . |
| 5,190,053 | 3/1993 | Meer . |
| 5,284,161 | 2/1994 | Karell . |
| 5,456,662 | 10/1995 | Edwards et al. . |
| 5,514,131 | 5/1996 | Edwards et al. . |
| 5,540,733 | 7/1996 | Testerman et al. . |
| 5,591,216 | 1/1997 | Testerman et al. . |
| 5,674,191 | 10/1997 | Edwards et al. . |
| 5,718,702 | 2/1998 | Edwards . |
| 5,792,067 | 8/1998 | Karell . |
| 5,843,021 | 12/1998 | Edwards et al. . |
| 5,897,579 | 4/1999 | Sanders . |
| 5,922,006 | 7/1999 | Sugerman . |
| 6,098,629 * | 8/2000 | Johnson et al. ...................... 128/897 |

OTHER PUBLICATIONS

Ellis P. D. M. et al., "Surgical relief of snoring due to palatal flutter; a preliminary report", *Annals of the Royal College of Surgeons of England*, vol. 75, No. 4, pp. 286–290 (1993).

Huang, L., "Flutter of Cantilevered Plates in Axial Flow", *Journal and Structures*, vol. 9, pp. 127–147 (1995).

Boot, H. et al., "Long–Term Results of Uvolopalatopharyngoplasty for Obstructive Sleep Apnea Syndrome", *The Laryngoscope*, pp. 469–475 (Mar. 2000).

Coleman, S. et al., "Midline Radiofrequency Tissue Reduction of the Palate for Bothersome Snoring and Sleep—Disordered Breathing; A Clinical Trial", *Otolaryngology—Head and Neck Surgery*, pp. 387–394 (Mar. 2000).

Fischer, Y. et al., "Die Radiofrequenzablation des weichen Gaumens (Somnoplastik)", *Redaktion*, pp. 33–40 (2000).

Kasey, K. et al., "Radiofrequency Volumetric Reduction of the Palate: An Extended Follow–Up Study", *Otolaryngology—Head and Neck Surgery*, vol. 122, N. 3, pp. 410–414 (Mar. 2000).

Dalmasso, F. et al., "Snoring: analysis, measurement, clinical implications and applications", *Euro Respir J.*, pp. 146–159 (1996).

Brochure, "Our Diagnostic Procedures are a Snap®!", *Snap Laboratories*, 4 pgs.

(List continued on next page.)

Primary Examiner—John P. Lacyk
Assistant Examiner—Brian Szmal
(74) Attorney, Agent, or Firm—Merchant & Gould P.C.

(57) ABSTRACT

A method and apparatus for treating snoring of a patient includes providing an implant for altering a dynamic response of a soft palate of the patient to airflow past the soft palate. The implant is embedded in the soft palate to alter the dynamic response. For example, the implant has a mass, stiffness or dampening sufficient to alter the dynamic response following the implantation without substantially impairing a function of the soft palate to close a nasal passage of the patient during swallowing.

21 Claims, 8 Drawing Sheets-

OTHER PUBLICATIONS

Brochure, "Snore—Free Nights—Guaranteed!", *Your Health News*, 2 pgs.

Brochure, "Snoreless™", *Nutrition for Life International*, 2 pgs. (Dec. 1999).

Brochure, "Haven't you Suffered from Snoring long enough", *Somnoplasty*$^{SM}$, 2 pgs.

Cole, P. et al., "Snoring: A Review and A reassessment", *The Journal of Otolaryngology*, vol. 24, No. 5, pp. 303–306 (1995).

Dalmasso, F. et al., "Snoring: analysis, measurement, Clinical implications and application", *Eur. Respir. J.*, vol. 9, pp. 146–159 (1996).

Harries, P.G. et al., "Review Article: The surgical treatment of snoring", *The Journal of Laryngology and Otology*, vol. 110, pp. 1105–1106 (Dec. 1996).

Huang, L. et al., "Biomechanics of snoring", *Endeavour*, vol. 19, No. 3, pp. 96–100 (1995).

Schwartz, R.S. et al., "Effects of electrical stimulation to the soft palate on snoring an obstructive sleep apnea", *J. Prosthet. Dent.*, vol. 76, No. 3, pp. 273–281 (1996).

Wiltfang, J. et al., "First results on daytime submadibular electrostimulation of suprahyoidal muscles to prevent lnight–time hypopharyngeal collapse in obstructive sleep apnea syndrome", *Int. J. Oral Maxillofac. Surg.*, vol. 28, pp. 21–25 (1999).

LaFrentz et al., "Palatal Stiffening Techniques for Snoring in a Novel Canine Model", Abstracts of the Twenty–Second Annual MidWinter Meeting of the Asociation for Research in Otolarlyngology, Abstract No. 499, vol. 22, pp. 125–126 (Feb. 13–18, 1999).

* cited by examiner

FIG. 1
FIG. 2
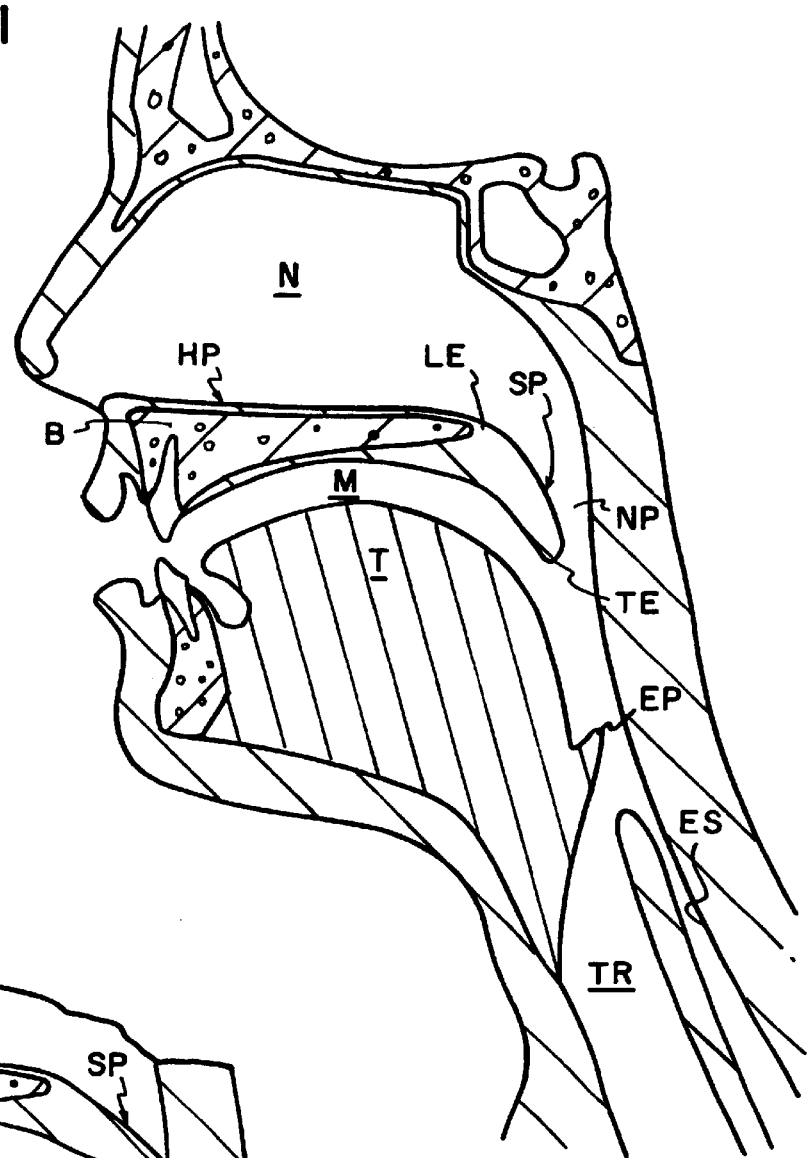
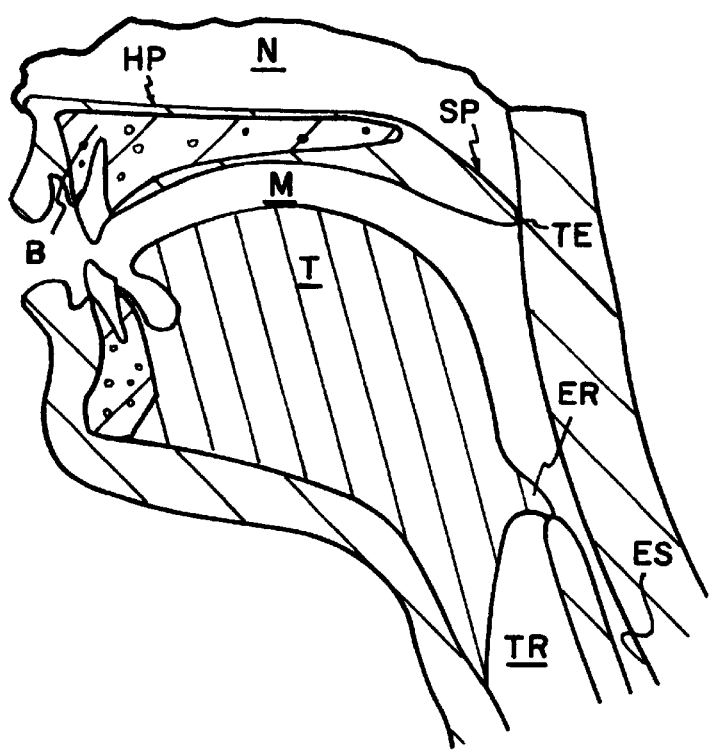

SNORING TREATMENT

BACKGROUND

1. Field of the Invention

This invention is directed to methods and apparatuses for treating snoring.

2. Description of the Prior Art

Snoring has received increased scientific and academic attention. One publication estimates that up to 20% of the adult population snores habitually. Huang, et al., "Biomechanics of Snoring", *Endeavour*, p. 96–100, Vol. 19, No. 3 (1995). Snoring can be a serious cause of marital discord. In addition, snoring can present a serious health risk to the snorer. In 10% of habitual snorers, collapse of the airway during sleep can lead to obstructive sleep apnea syndrome. Id.

Notwithstanding numerous efforts to address snoring, effective treatment of snoring has been elusive. Such treatment may include mouth guards or other appliances worn by the snorer during sleep. However, patients find such appliances uncomfortable and frequently discontinue use (presumably adding to marital stress).

Electrical stimulation of the soft palate has been suggested to treat snoring and obstructive sleep apnea. See, e.g., Schwartz, et al., "Effects of electrical stimulation to the soft palate on snoring and obstructive sleep apnea", *J. Prosthetic Dentistry*, pp. 273–281 (1996). Devices to apply such stimulation are described in U.S. Pat. Nos. 5,284,161 and 5,792,067. Such devices are appliances requiring patient adherence to a regimen of use as well as subjecting the patient to discomfort during sleep. Electrical stimulation to treat sleep apnea is discussed in Wiltfang, et al., "First results on daytime sub mandibular electro stimulation of suprahyoidal muscles to prevent night-time hypopharyngeal collapse in obstructive sleep apnea syndrome", *International Journal of Oral & Maxillofacial Surgery*, pp. 21–25 (1999).

Surgical treatments have been employed. One such treatment is uvulopalatopharyngoplasty. In this procedure, so-called laser ablation is used to remove about 2 cm of the trailing edge of the soft palate thereby reducing the soft palate's ability to flutter between the tongue and the pharyngeal wall of the throat. The procedure is frequently effective to abate snoring but is painful and frequently results in undesirable side effects. Namely, removal of the soft palate trailing edge comprises the soft palate's ability to seal off nasal passages during swallowing and speech. In an estimated 25% of uvulopalatopharyngoplasty patients, fluid escapes from the mouth into the nose while drinking. Huang, et al., supra at 99. Uvulopalatopharyngoplasty (UPPP) is also described in Harries, et al., "The Surgical treatment of snoring", *Journal of Laryngology and Otology*, pp.1105–1106 (1996) which describes removal of up to 1.5 cm of the soft palate. Assessment of snoring treatment is discussed in Cole, et al., "Snoring: A review and a Reassessment", *Journal of Otolaryngology*, pp. 303–306 (1995).

Huang, et al., supra, describe the soft palate and palatal snoring as an oscillating system which responds to airflow over the soft palate. Resulting flutter of the soft palate (rapidly opening and closing air passages) is a dynamic response generating sounds associated with snoring. Huang, et al., propose an alternative to uvulopalatopharyngoplasty. The proposal includes using a surgical laser to create scar tissue on the surface of the soft palate. The scar is to reduce flexibility of the soft palate to reduce palatal flutter. Huang, et al., report initial results of complete or near-complete reduction in snoring and reduced side effects.

Surgical procedures such as uvulopalatopharyngoplasty and those proposed by Huang, et al., continue to have problems. The area of surgical treatment (i.e., removal of palatal tissue or scarring of palatal tissue) may be more than is necessary to treat the patient's condition. Surgical lasers are expensive. The proposed procedures are painful with drawn out and uncomfortable healing periods. The procedures have complications and side effects and variable efficacy (e.g., Huang, et al., report promising results in 75% of patients suggesting a full quarter of patients are not effectively treated after painful surgery). The procedures may involve lasting discomfort. For example, scar tissue on the soft palate may present a continuing irritant to the patient. Importantly, the procedures are not reversible in the event they happen to induce adverse side effects not justified by the benefits of the surgery.

SUMMARY OF THE INVENTION

According to a preferred embodiment of the present invention, methods and apparatuses are disclosed for treating snoring of a patient. The invention includes providing an implant for altering a dynamic response of a soft palate of the patient to airflow past the soft palate. The implant is embedded in the soft palate to alter the dynamic response. For example, the implant has a mass, stiffness or dampening sufficient to alter the dynamic response following the implantation without substantially impairing a function of the soft palate to close a nasal passage of the patient during swallowing.

BRIEF DESCRIPTION OF THE DRAWINGS

FIG. 1 is a side sectional view of a portion of a human head showing a soft palate in a relaxed state and in relation in adjacent anatomical features;

FIG. 2 is a portion of the view of FIG. 1 showing the soft palate in a flexed state;

DESCRIPTION OF THE PREFERRED EMBODIMENT

For ease of understanding the present invention, the dynamics of snoring are explained with reference to FIGS. 1–4. The hard palate HP overlies the tongue T and forms the roof of the mouth M. The hard palate HP includes a bone support B and does not materially deform during breathing. The soft palate SP is soft and is made up of mucous membrane, fibrous and muscle tissue extending rearward from the hard palate HP. A leading end LE of the soft palate SP is anchored to the trailing end of the hard palate HP. A trailing end TE of the soft palate SP is unattached. Since the soft palate SP is not structurally supported by bone or hard cartilage, the soft palate SP droops down from the plane of the hard palate HP in an arcuate geometry of repose.

The pharyngeal airway passes air from the mouth M and the nasal passages N into the trachea TR. The portion of the pharyngeal airway defined between opposing surfaces of the upper surface of the soft palate SP and the wall of the throat is the nasopharynx NP.

During normal breathing, the soft palate SP is in the relaxed state shown in FIG. 1 with the nasopharynx NP unobstructed and with air free to flow into the trachea TR from both the mouth M and the nostrils N.

During swallowing, the soft palate SP flexes and extends (as shown in FIG. 2) to close the nasopharynx NP thereby preventing fluid flow from the mouth M to the nasal passages N. Simultaneously, the epiglottis EP closes the trachea TR so that food and drink pass only into the esophagus ES and not the trachea TR. The soft palate SP is a valve to prevent regurgitation of food into the nose N. The soft palate SP also regulates airflow through the nose N while talking. Since the soft palate SP performs such important functions, prior art techniques for surgically altering the soft palate SP can compromise these functions.

The majority of snoring is caused by the soft palate SP flapping back and forth. If breathing is solely through the nose N with the mouth closed, the trailing edge TE of the soft palate SP is sucked into the nasopharyngeal space NP obstructing the airway and subsequently falls opening the airway in a repeating cycle. When the mouth is open, air flows over the upper and lower surfaces of the soft palate SP causing the soft palate SP to flap up and down alternating in obstructing the oral and nasal passageways M, N. The snoring sound is generated by impulses caused by rapid obstruction and opening of airways. Huang, et al., state the airway passage opening and closing occurs 50 times per second during a snore. Huang, et al., utilize a spring-mass model (FIG. 5) to illustrate oscillation of the soft palate in response to airflow (where the soft palate is the ball B of mass depending by a spring S from a fixed anchor A).

Figure 3:
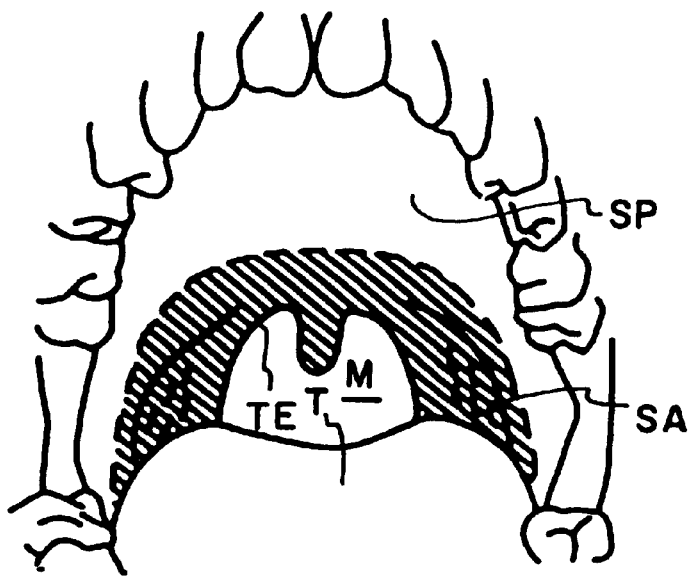
FIG. 3 is a front view of an interior of the mouth shown in FIG. 1 and showing an area to be ablated according to a first prior art surgical procedure.
Figure 4:
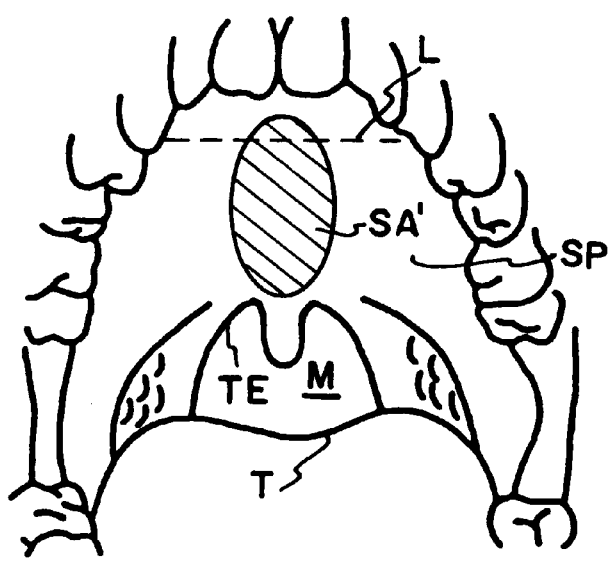
FIG. 4 is the view of FIG. 3 and showing an area to be scarred according to a second prior art surgical procedure.

Huang, et al., analogize the shortening of the soft palate SP in uvulopalatopharyngoplasty as effectively raising the critical air flow speed at which soft palate flutter will occur. The shaded area SA in FIG. 3 shows the area of the trailing end TE of the soft palate SP to be removed during this procedure. The alternative procedure proposed by Huang, et al., reduces the flexibility of the soft palate SP through surface scarring which is asserted as effecting the critical flow speed. The shaded area SA' in FIG. 4 shows the area to be scarred by this alternate procedure. In FIG. 4, dashed line L shows the demarcation between the soft and hard palates.

Figure 5:
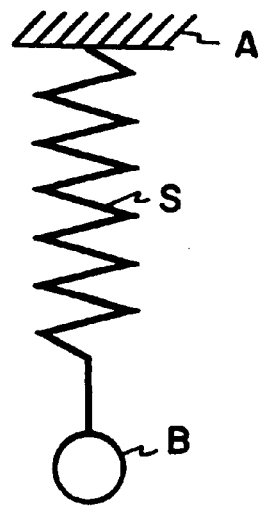
FIG. 5 is a schematic representation of a spring-mass system model of the soft palate.

Using the spring-mass model of FIG. 5 as a convenient model of the soft palate SP, the present invention is directed to a surgical implant into the soft palate SP to alter the elements of the model and thereby alter the dynamic response of the soft palate SP to airflow. The implant can alter the mass of the model (the ball B of FIG. 5), the spring constant of the spring S, the dampening of the spring S or any combination of these elements. Unlike the prior art surgical techniques, the implants that will be described are easy to insert in a small incision resulting in reduced patient discomfort and are not exposed to the interior of the mouth (such as the surface scarring of Huang, et al.) as a patient irritant. Also, as will be described, the degree of dynamic remodeling can be fine tuned avoiding the need for excessive anatomical modification and are reversible in the event of adverse consequences.

Figure 6:
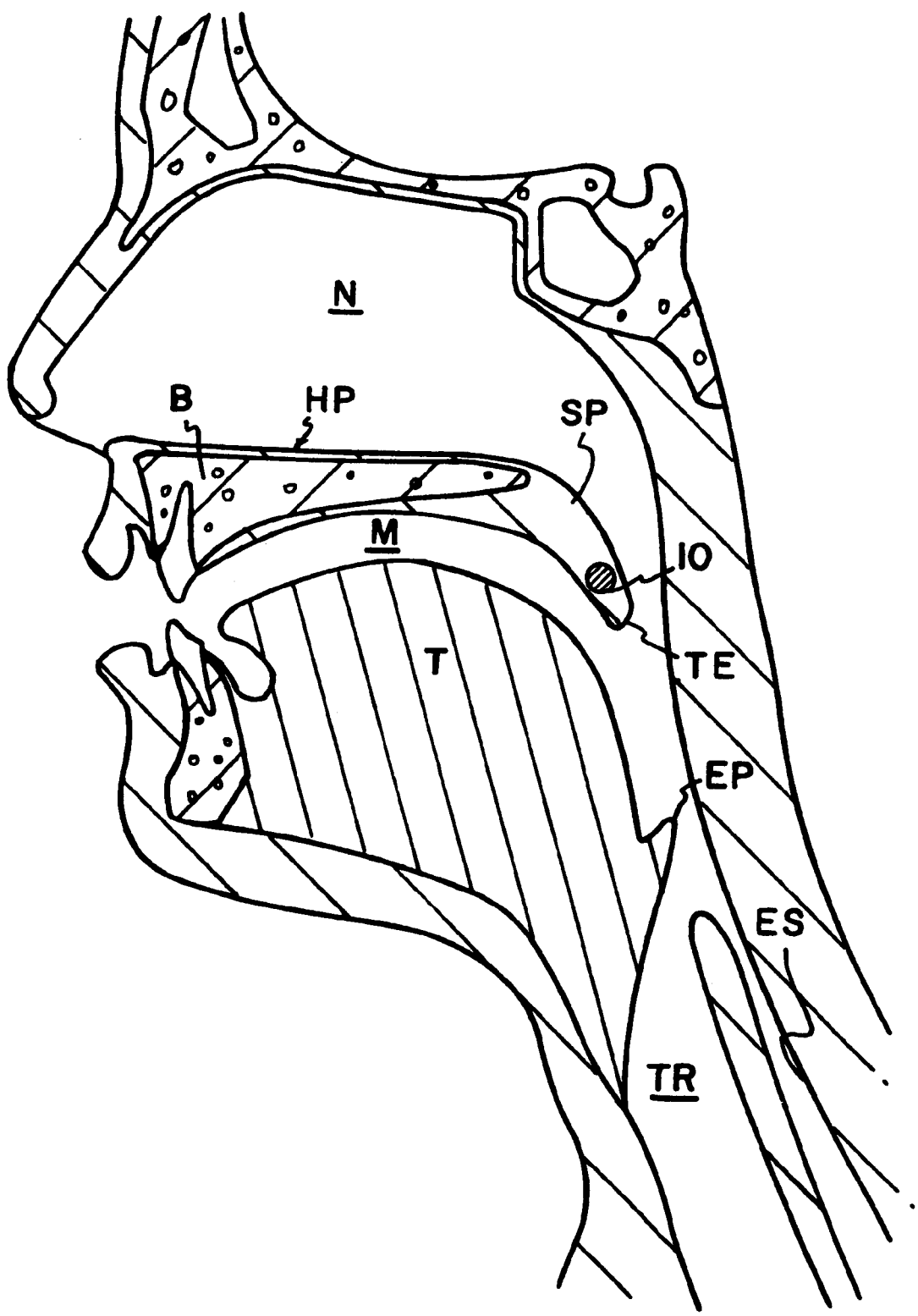
FIG. 6 is the view of FIG. 1 with the soft palate containing an implant according to a first embodiment of the present invention.
Figure 7:
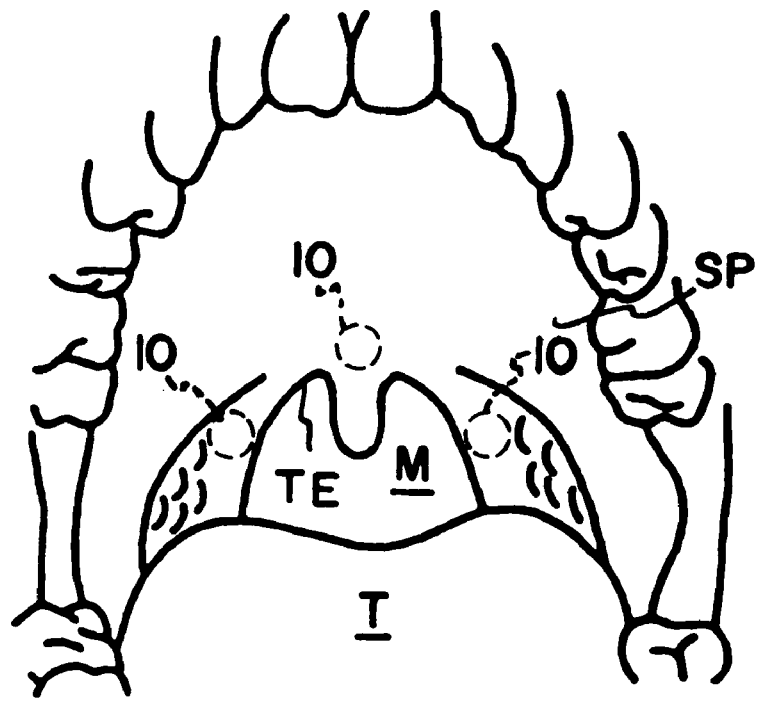
FIG. 7 is the view of FIG. 3 showing the embodiment of FIG. 6.
Figure 8:
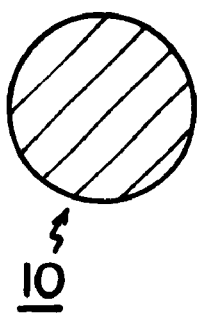
FIG. 8 is a cross-sectional view of the implant of FIG. 6.

FIGS. 6–7 illustrate a first embodiment of the present invention where individual units 10 of mass (in the form of implantable modular devices such as spheres or implants of other geometry) are imbedded in the soft palate SP in close proximity to the trailing end TE. With reference to the model of FIG. 5, the spheres add mass to the mass-spring system thereby altering dynamic response to airflow and adding resistance to displacement and accelerating. The placement of the units 10 of mass also alter the location of the soft palate's center of mass further altering the model and dynamic response.

The embodiment of FIGS. 6–10 is tunable to a particular patient in that multiple modules 10 can be implanted (as illustrated in FIG. 7). This permits the surgeon to progressively increase the number of implanted modules 10 until the altered dynamic response is such that snoring inducing oscillation is abated at normal airflow. The individual modules 10 may be placed into the soft palate SP through small individual incisions closed by sutures which is much less traumatic than the gross anatomical destruction of uvulopalatopharyngoplasty or the large surface area scarring proposed by Huang, et al.

Preferably, such modules 10 of mass are solid modules such as spheres of biocompatible material which are radiopaque (or radio-marked) and compatible with magnetic resonance imaging (MRI). Titanium is such a material. By way of non-limiting example, the modules 10 of mass may be about 2–4 mm in diameter. In the case of pure, non-sintered titanium, each such sphere 10 would add . 15–1.22 gm of mass to the trailing end TE of the soft palate SP and contribute to re-modeling the mass distribution of the soft palate SP. An example of an alternative material is any biocompatible ceramic.

Figure 9:
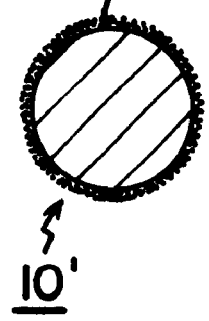
FIG. 9 is a first modification of the implant of FIG. 8 having a tissue in-growth layer.

As shown in FIG. 9, the spheres (labeled 10' to distinguish from the version 10 of FIG. 8) may be sintered throughout or otherwise provided with tissue growth inducing material 12 on their outer surface. Such material may be a sintered outer layer or a coating or covering such as a polyester fabric jacket. Such material permits and encourages tissue in-growth to secure the implant 10' in place. Also, placement of an implant 10 or 10' will induce a fibrotic response acting to stiffen the soft palate SP (and further alter the dynamic response and resistance to displacement and acceleration). A sintered or coated sphere 10' will enhance the fibrotic response and resulting stiffening.

Figure 10:
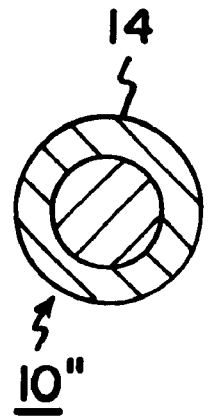
FIG. 10 is a second modification of the implant of FIG. 8 having a smooth outer layer.

While tissue in-growth and enhanced fibrotic response have the benefits described above, such embodiments may make the implant 10' more difficult to remove in the event reversal of the procedure is desired. Therefore, as shown in FIG. 10 as an alternative, the spheres (labeled 10" to distinguish from the implants 10, 10') may be coated with smooth coating 14 (such as parylene or PTFE) to reduce fibrosis.

The embodiments of FIGS. 6–10 add to and relocate the mass of the spring-mass system of FIG. 5 to remodel the dynamic response. The amount of mass is selected to alter the dynamic response but not preclude the soft palate SP being moved to close off nasal passages N during swallowing. Through fibrotic response and incision healing, the spring S of the model is stiffened.

In addition to modifying the mass profile of the spring-mass system, the spring component S of FIG. 5 can be modified (alone or in combination with mass modification) to alter dynamic response. FIGS. 11–16 illustrate an implant 20 in the form of a flexible strip for placement in the soft palate. The use of the term "strip" herein is not intended to be limited to long, narrow implants but can also include plates or other geometries implanted to alter the dynamic model of the soft palate SP. Elongated strips are presently anticipated as a preferred geometry to facilitate ease of implant.

Figure 11:
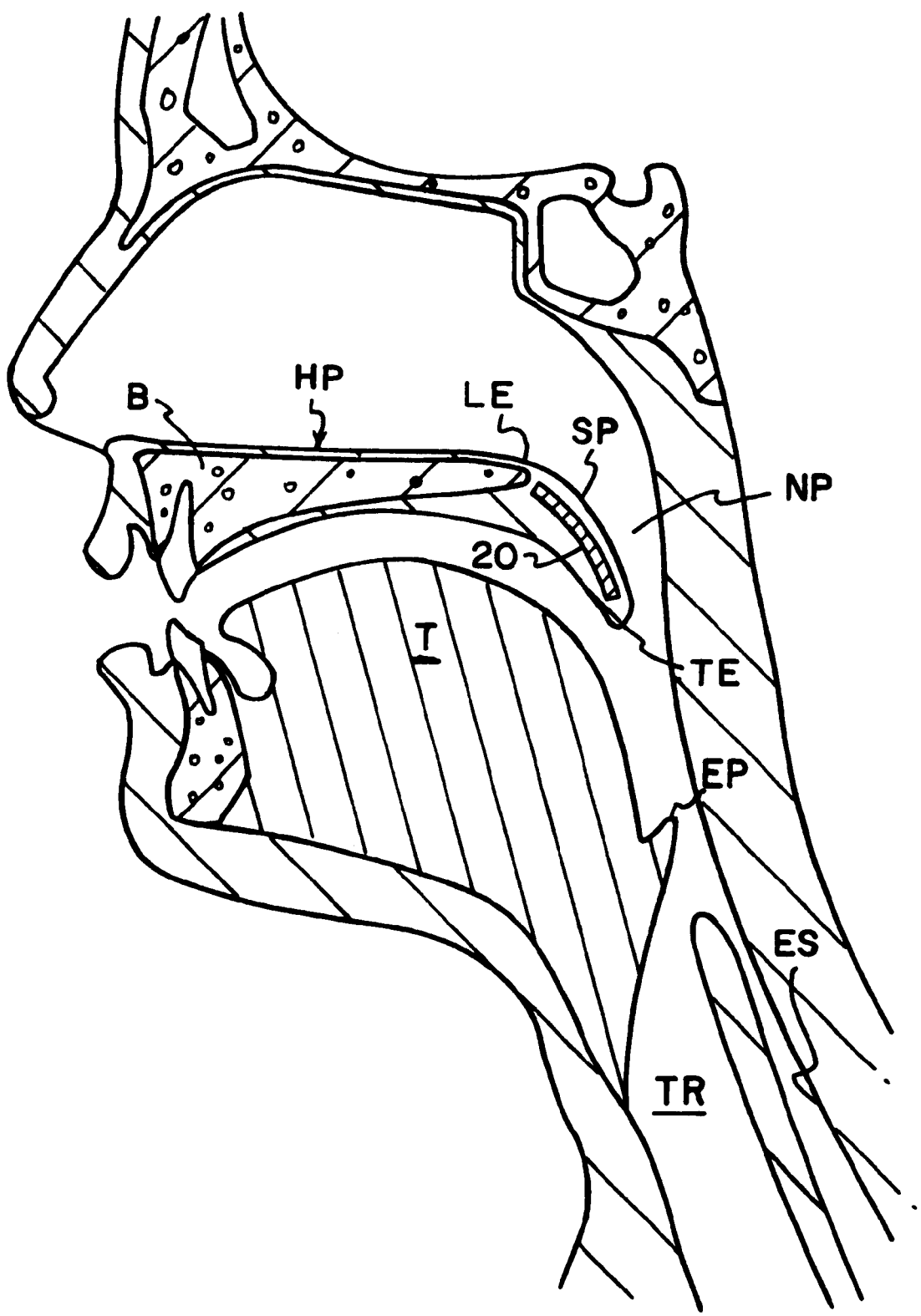
FIG. 11 is the view of FIG. 6 with the soft palate containing an implant according to a second embodiment of the present invention.
Figure 12:
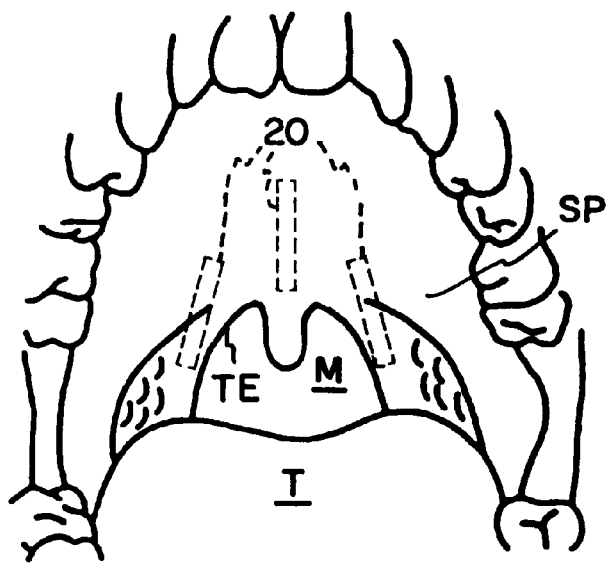
FIG. 12 is the view of FIG. 7 showing the embodiment of FIG. 11.

The strip 20 has a transverse dimension less than a longitudinal dimension. By way of non-limiting example, the strip may have a length $L_s$ of about 20–30 mm, a thickness $T_s$ of about 2–4 mm and a width $W_s$ of 5–10 mm. As shown in FIG. 11, the strip 20 is embedded in the soft palate SP with the longitudinal dimension $L_s$ extending from adjacent the hard palate HP toward the trailing end TE of the soft palate SP. As shown in FIG. 12, multiple strips 20 may be embedded in the soft palate SP extending either straight rearward or angled to the sides while extending rearward. The strips 20 may be formed straight (FIG. 14) or pre-shaped (FIG. 15) to have a rest shape approximate to the side-cross section shape of the soft palate in a relaxed state.

Figure 16:
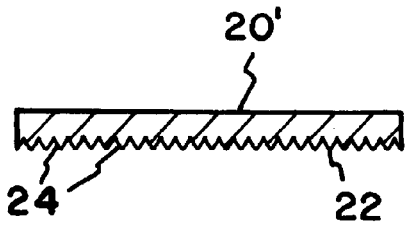
FIG. 16 is the view of FIG. 14 with the implant constructed to have greater flexion in a downward direction.

The strips 20 may be any flexible, biocompatible material and are preferably radiopaque or radio-marked as well as MRI compatible. The strips 20 need not be elastic and having a material spring constant biasing them to their original shape. Such strips 20 could simply be flexible, plastically deformable strips which are stiffer than the soft palate SP to reinforce the soft palate SP and assist the soft palate SP in resisting deflection due to airflow. Such stiffening of the soft palate SP stiffens the spring S in the spring-mass system of FIG. 5 and alters the dynamic response of the soft palate SP. The strip 20 may be a spring having a spring constant to further resist deflection of the soft palate SP as well as urging the soft palate SP to the relaxed state of FIG. 5. The stiffness of the strip 20, a spring constant of the strip 20, and the number of strips 20, are selected to avoid preclusion of closure of the soft palate SP during swallowing. Examples of suitable materials include titanium and nitinol (a well-known nickel-titanium alloy). As with the examples of FIGS. 9 and 10, the strips 20 may be provided with tissue in-growth surfaces or may be coated as desired. Also, the strips may be structurally modified to control their flexibility. In FIG. 16, the bottom 22 of the strip 20 (facing the tongue after placement) is provided with transverse notches 24 to enhance downward flexion of the strip 20 relative to upward flexion of the strip 20 following placement.

Figure 13:
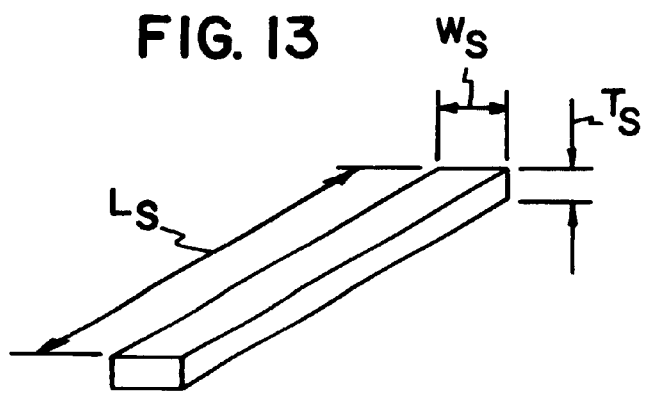
FIG. 13 is a perspective view of the implant of FIG. 11.
Figure 14:
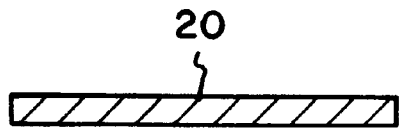
FIG. 14 is a cross-sectional view of the implant of FIG. 13.
Figure 15:
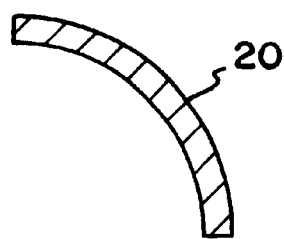
FIG. 15 is a view of the implant of FIG. 14 with the implant pre-formed to assume the shape of a soft palate in a relaxed state.
Figure 17:
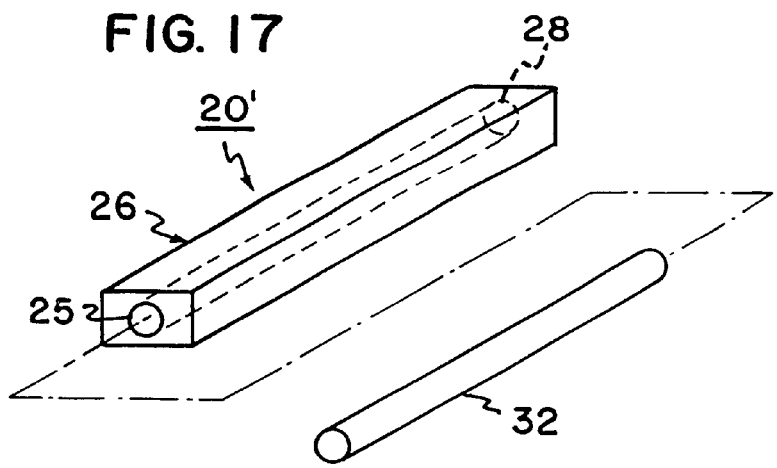
FIG. 17 is an exploded perspective view of first modification of the implant of FIG. 13.

FIG. 17 provides an alternative to the strips 20 of FIG. 13. In FIG. 17, the strip 20' includes a housing 26 having an interior space 28 with an access opening 25. The interior space 28 extends in the longitudinal dimension of the housing 26. The strip 20' further includes a longitudinal insert 32 sized to be passed through the access opening 25 and into the space 28. By way of non-limiting example, the housing 26 could be silicone rubber (with radio-markers, not shown, to indicate placement) and the inserts 32 could be titanium rods or other flexible member. With the embodiment of FIG. 17, the housing 26 (without an insert) may be embedded in the soft palate SP. The housing 26 acts independently as a stiffening strip to add stiffness to the soft palate SP to alter the soft palate's dynamic response. In the event further stiffening or a spring action is desired, the implant 20' can be selectively tuned to the patient's unique dynamic model by placing the insert 32 into the space 28 at the time of initial surgery or during a subsequent procedure. The embodiment of FIG. 17, permits selection of an insert 32 from a wide variety of materials and construction so that an insert 32 of desired characteristics (e.g., stiffness and spring action) can be selected to be inserted in the space 28 and alter the dynamic response as desired. The embodiment of FIG. 17 also permits later removal of the insert 32 and replacement with a different insert 32 of different properties for post-surgery modification of the soft palate's dynamic response.

Figure 18:
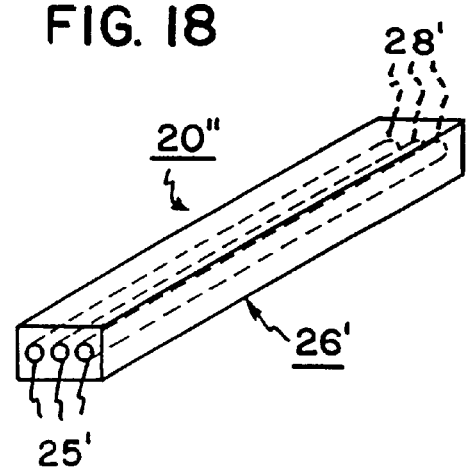
FIG. 18 is a perspective view of a modification of a housing of the embodiment of FIG. 17.

The embodiment of FIG. 18 is similar to that of FIG. 17. The housing 26' is provided with multiple, parallel-aligned interior spaces 28' and access openings 25'. In addition to the function and benefits of the embodiment of FIG. 17, the number of inserts 32 may be varied to alter and adjust the dynamic response of the soft palate SP.

Figure 19:
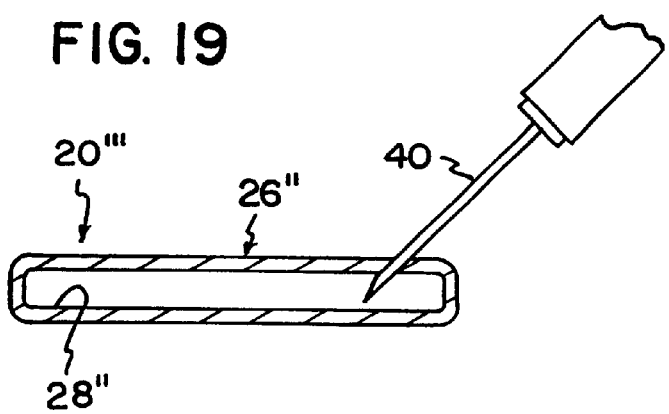
FIG. 19 is a side section view of a second modification of the implant of FIG. 13.
Figure 20:
FIG. 20 is a cross-sectional view of an implant that is another embodiment of the present invention, the implant is shown in a flattened orientation.

FIG. 19 illustrates a still further embodiment of the strip implant. In FIG. 19, the strip 20''' is a bladder having a housing 26'' in the form of a completely sealed envelope of flexible synthetic material defining an interior space 28''. The envelope 26'' is preferably self-sealing following needle injection. Fluid is injected into the housing 26'' (e.g., through hypodermic needle 40 injection) to stiffen the strip 20'''. Addition of fluid further stiffens the strip 20''' and further alters the dynamic response of the soft palate SP. Removal of fluid increases the flexibility. Unlike the embodiments of FIG. 17 (where inserts 32 are most effectively replaced post-operatively through incision to alter flexibility), the embodiment of FIG. 19 permits selectively varying flexibility of the soft palate SP through needle injection. An alternative to FIG. 19 is to fill the space 28'' with a so-called phase change polymer and inject a stiffening agent into the space 28'' to alter the flexibility of the polymer.

FIGS. 20–23 illustrate a still further embodiment of the present invention. In the foregoing embodiments, the spring-mass system of FIG. 5 is altered by altering the mass of the soft palate SP or the spring characteristics of the soft palate SP. The dynamic response can also be altered by altering the force acting on the spring-mass system. Namely, the force acting on the soft palate SP is generated by airflow over the surface of the soft palate. The soft palate acts as an airfoil which generates lift in response to such airflow. By modifying the longitudinal (i.e., anterior to posterior) cross-sectional geometry of the soft palate SP, the aerodynamic response and, accordingly, the dynamic response are altered.

Figure 21:
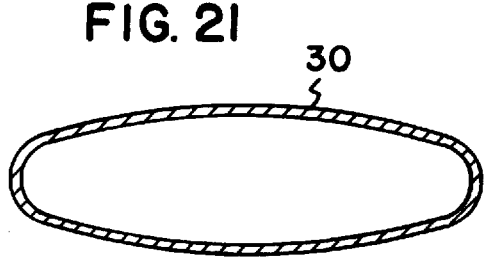
FIG. 21 is a cross-sectional view of the implant of FIG. 20 in an expanded orientation.
Figure 22:
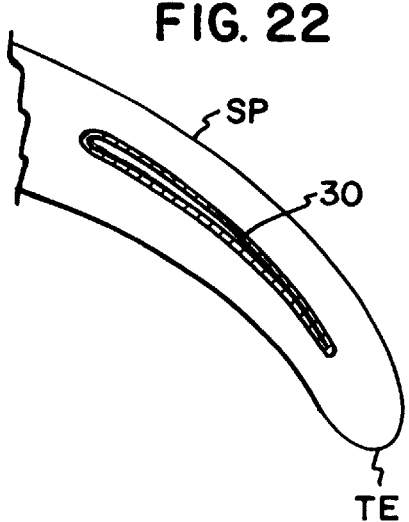
FIG. 22 shows the implant of FIG. 20 in the flattened orientation and implanted in the soft palate.
Figure 23:
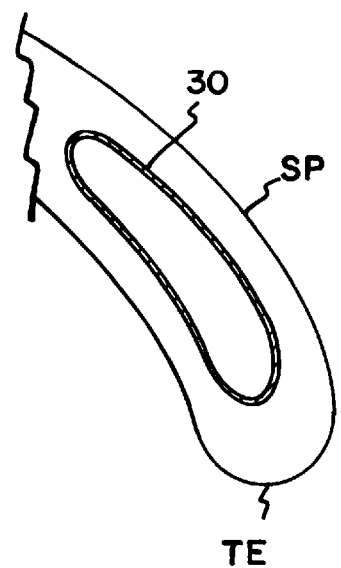
FIG. 23 shows the implant in FIG. 21 in the expanded orientation and implanted in the soft palate.

In the embodiments of FIGS. 20–23, the implant 30 is inserted into the soft palate SP through an incision. The implant 30 has an oval shape to cause deformation of the geometry of the soft palate SP. Prior to implantation, the implant 30 is preferably formed as a flat oval (FIGS. 20 and 22) for ease of insertion. After implantation, the implant 30 expands to an enlarged oval (FIG. 21 and 23). While such expansion could be accomplished mechanically (i.e., through balloon expansion), the implant 30 is preferably formed as a shape-memory alloy (such as nitinol) which expands to the enlarged shape in response to the warmth of the body. In addition to changing the aerodynamics of the soft palate SP, the implant 30 can be constructed with a mass and stiffness as desired to alter the spring and mass components of the spring-mass system of FIG. 5.

The foregoing describes numerous embodiments of an invention for an implant for the soft palate to alter a dynamic response of the soft palate. The invention is much less traumatic than prior surgical treatments. Further, the invention permits use of reversible procedures as well as procedures which can be selectively tuned both during surgery and post-operatively. Having described the invention, alternatives and embodiments may occur to one of skill in the art. For example, the strips of FIG. 13 may be encased coiled springs which may be tightened to further stiffen the strips. Such strips may also be hinged segments. It is intended that such modifications and equivalents shall be included within the scope of the following claims.

What is claimed is:

1. A method for treating snoring of a patient, said method comprising:
   selecting an implant dimensioned so as to be implanted into a soft palate of said patient, said implant having mechanical characteristics for said implant, at least in combination with a fibrotic tissue response induced by said implant, to alter a dynamic response of said soft palate of said patient to air flow past said soft palate without application of force external to said soft palate;
   implanting said implant into said soft palate to alter said dynamic response.

2. A method according to claim 1 comprising providing said implant to have a mass sufficient to alter said dynamic response following said implantation without substantially impairing a function of said soft palate to close a nasal passage of said patient from a pharynx of said patient during swallowing.

3. A method according to claim 1 comprising providing said implant to dampen said dynamic response following said implantation without substantially impairing a function of said soft palate to close a nasal passage of said patient from a pharynx of said patient during swallowing.

4. A method according to claim 1 comprising providing said implant to stiffen said soft palate to alter said dynamic response following said implantation without substantially impairing a function of said soft palate to close a nasal passage of said patient from a pharynx of said patient during swallowing.

5. A method treating snoring of a patient, said method comprising:
   selecting an implant dimensioned so as to be implanted into a soft palate of said patient, said implant having mechanical characteristics for said implant, at least in combination with a fibrotic tissue response induced by said implant, to alter a dynamic response of said soft palate of said patient in response to air flow past said soft palate without application of force external to said soft palate, and said implant having a longitudinal dimension and a narrower transverse dimension and said implant being flexible along said longitudinal dimension, said implant further dimensioned so as to not substantially increase a bulk of said soft palate following implantation of said implant into said soft palate; and
   implanting said implant within said soft palate to alter said dynamic response with said longitudinal dimension extending in a path generally from a front of said patient toward a back of said patient.

6. A method for treating snoring of a patient, said method comprising:
   selecting an implant dimensioned so as to be implanted into a soft palate of said patient, said implant having mechanical characteristics for said implant, at least in combination with a fibrotic tissue response induced by said implant, to alter a dynamic response of said soft palate of said patient in response to air flow past said soft palate without application of force external to said soft palate, and said implant having a longitudinal dimension and a narrower transverse dimension and said implant being flexible along said longitudinal dimension, and said implant having a stiffness selected to stiffen said soft palate to alter said dynamic response following said implantation without substantially impairing a function of said soft palate to close a nasal passage of said patient from a pharynx of said patient during swallowing, said implant further dimensioned so as to not substantially increase a bulk of said soft palate following implantation of said implant into said soft palate; implanting said implant within said soft palate to alter said dynamic response with said longitudinal dimension extending in a path generally from a front of said patient toward a back of said patient.

7. A method according to claim 6 wherein said stiffness is adjustable.

8. A method according to claim 7 wherein said implant includes a housing having an interior space to receive a selected one of a plurality of inserts of varying stiffness.

9. A method according to claim 7 wherein said implant includes a housing having an interior space to receive a selected number of a plurality of inserts.

10. A method according to claim 7 wherein said implant is a bladder having an enclosed interior volume to receive a selected amount of a fluid to alter a stiffness of said bladder in response to an amount of said fluid in said volume.

11. A method according to claim 7 wherein said implant is a bladder having an enclosed interior volume containing a fluid with a stiffness of said bladder adjustable in response to a stiffening agent admitted to said fluid.

12. A method according to claim 5 wherein said implant is configured to a greater deflection resistance in one direction than in an opposite direction.

13. A method according to claim 5 wherein said implant has a spring constant selected to stiffen said palate.

14. A method according to claim 1 wherein said implant is dimensioned to expand a geometry of the soft palate by an amount sufficient to alter an aerodynamic response to airflow over the soft palate.

15. An apparatus for treating snoring of a patient suffering from snoring attributable, at in least in part, to a snoring sound generating oscillation of a soft palate of said patient in response to airflow past said soft palate and where said soft palate has a characteristic dynamic response to said airflow prior to treatment, said apparatus comprising:

an implant of bio-compatible material sized to be embedded within said soft palate;

said implant having mechanical characteristics for said implant, at least in combination with a fibrotic tissue response induced by said implant and without application of force external to said soft palate, to alter said dynamic response without substantially impairing a function of said soft palate to close a nasal passage of said patient from a pharynx of said patient during swallowing; and said implant being flexible along said longitudinal dimension, and said implant not susceptible to substantial expansion and contraction in response to contraction and relaxation of muscles of the soft palate.

16. An apparatus according to claim 15 wherein said implant includes a surface adapted for tissue in-growth.

17. An apparatus according to claim 16 wherein at least an outer surface of said implant is a polyester.

18. An apparatus according to claim 15 wherein said implant is elastic to be biased toward a rest position following bending of said implant along said longitudinal axis.

19. An apparatus according to claim 15 wherein said implant includes a radiopaque marking.

20. An apparatus according to claim 15 wherein said implant includes a housing with inserts for varying a stiffness of said implant.

21. An apparatus according to claim 15 wherein said implant is an injectable polymer injected into said soft palate.

* * * * *